US007838281B2

(12) United States Patent
Kraus et al.

(10) Patent No.: US 7,838,281 B2
(45) Date of Patent: Nov. 23, 2010

(54) SULFIDE BATH

(75) Inventors: David W. Kraus, Birmingham, AL (US); Jerome E. Brisson, Chaplin, CT (US)

(73) Assignee: Soothing Sulfur Spas, LLC, Chaplin, CT (US)

( * ) Notice: Subject to any disclaimer, the term of this patent is extended or adjusted under 35 U.S.C. 154(b) by 785 days.

(21) Appl. No.: 11/652,836

(22) Filed: Jan. 12, 2007

(65) Prior Publication Data

US 2008/0170968 A1 Jul. 17, 2008

(51) Int. Cl.
*C12M 1/36* (2006.01)
*C12M 1/38* (2006.01)
*C12M 3/00* (2006.01)

(52) U.S. Cl. ........................ 435/286.1; 210/85; 422/108

(58) Field of Classification Search .............. 435/286.1; 422/108; 210/85
See application file for complete search history.

(56) References Cited

U.S. PATENT DOCUMENTS 2,558,912 A 7/1951 Radelicki .................... 128/368
4,011,072 A 3/1977 Holman et al.
5,288,311 A 2/1994 Furutani
5,347,665 A 9/1994 Kumon
5,422,014 A 6/1995 Allen ......................... 210/743
5,454,918 A 10/1995 Javadi et al.
5,505,847 A 4/1996 Yamada ................. 210/167.13
6,125,481 A 10/2000 Sicilano ......................... 4/509
6,164,632 A 12/2000 Uchida ....................... 261/102
6,340,431 B2 1/2002 Khan .......................... 210/85
6,461,498 B2 10/2002 Tseng ......................... 210/87
6,530,964 B2 * 3/2003 Langer et al. ................. 44/301
6,581,220 B2 6/2003 Yekutiely ....................... 4/661
6,724,873 B2 4/2004 Senna Da Silva ...... 379/102.01

FOREIGN PATENT DOCUMENTS

CN 1236611 A * 12/1999
JP 62-171723 7/1987

(Continued)

OTHER PUBLICATIONS

David W. Kraus, et al., "Sulfide Consumption by Mussel Gill Mitochondria is not Strictly Tied to Oxygen Reduction: Measurements Using a Novel Polargraphic Sulfide Sensor" Jul. 26, 2004.

(Continued)

*Primary Examiner*—Walter D Griffin
*Assistant Examiner*—Shanta G Doe
(74) *Attorney, Agent, or Firm*—McCormick, Paulding & Huber LLP

(57) ABSTRACT

An apparatus for establishing a sulfide bath includes a sulfide supply means for introducing sulfide into water for a water bath, a water chemistry monitoring means for monitoring at least a sulfide concentration of water from the water bath, an electronic controller connected with the sulfide supply means and the water chemistry monitoring means, wherein the electronic controller is configured to control the sulfide supply means to regulate the sulfide concentration in the water bath based on input from the water chemistry monitoring means. A variation of the apparatus is portable and can be used in connection with existing water baths. Another variation of the apparatus is for preserving biological materials.

27 Claims, 7 Drawing Sheets

FOREIGN PATENT DOCUMENTS

| | | | |
|---|---|---|---|
| JP | 63-088095 | | 4/1988 |
| JP | 01-097459 | | 4/1989 |
| JP | 06-039014 | | 2/1994 |
| JP | 06-154279 | | 6/1994 |
| JP | 06-154280 | | 6/1994 |
| JP | 8-1173 | | 1/1996 |
| JP | 2006-061332 | * | 3/2006 |
| WO | 2006/047086 | | 5/2006 |

OTHER PUBLICATIONS

Written Opinion and International Search Report for Serial No. PCT/US2008/000340 dated Apr. 29, 2008.

* cited by examiner

SULFIDE BATH

FIELD OF THE INVENTION

This invention relates to the establishment and maintenance of chemical baths for therapeutic, scientific and medical purposes.

BACKGROUND OF THE INVENTION

Hydrogen sulfide ($H_2S$), most commonly known as the source of the rotten egg odor, is now known to play important roles in mammalian cell signaling. These include regulation of vascular smooth muscle tone, neuronal activity, liver bile production and general cell protection from the oxidative stress of aerobic metabolism. Because of the potential toxicity of $H_2S$, its cellular/organismal concentration is tightly regulated by enzymatic production and consumption pathways so that toxic levels are not reached. However, too little $H_2S$, equivalent to too little reducing power and consequently too much oxidative stress, has been linked to numerous degenerative pathologies such as cardiovascular disease, rheumatoid arthritis, Alzheimer's type dementia, various cancers, and aging in general. Many of these and other pathologies result from the accumulation of cellular oxidative damage that, as is now known from numerous studies, could well be limited by antioxidants or reductants such as vitamins E, B and C and the beneficial phytochemicals associated with fresh vegetables and fruit, as well as $H_2S$.

One way in which $H_2S$ may achieve these beneficial effects is by acting as a global cellular and organismal reductant, capable of shifting the cellular reductive/oxidative (redox) balance towards the reduced state and protecting against oxidative damage. Major sites of cellular oxidative damage include thiol groups on proteins, represented as PROTEIN-SH, or RSH where R is the protein. Protein thiols can become oxidized and linked as dithiol bonds (RS—SR), or bound to nitric oxide, NO, as RSNO, both of which can dramatically limit protein function and hence normal cellular activity. $H_2S$ along with other cellular reductants such as glutathione serve to reduce protein dithiols, or RSNOs, to reestablish protein function. Most cellular reductants are larger molecules compared to $H_2S$ and therefore cannot diffuse as rapidly, readily pass through cell membranes, or fit into smaller molecular spaces where some oxidized thiols occur. Therefore $H_2S$ may be one of the most important cellular defenses against oxidative stress.

$H_2S$ is regularly produced by human cellular metabolism, and can be augmented by dietary components that provide substrates for $H_2S$-producing metabolic pathways. $H_2S$ production can also be augmented by the important but underutilized and understudied method of bathing in warm sulfur mineral springs, termed sulfur balneotherapy. Sulfur mineral springs are often highly valued for their healing qualities, most likely as a result of significant levels of $H_2S$ that are absorbed through the skin to help recharge cellular redox status. Scientific investigations of the effects of warm sulfur mineral springs are beginning to be published demonstrating benefits in a number of pathologies including cardiovascular degeneration, skin ailments, wounds, breathing difficulties, rheumatoid arthritis, hepatic, gall bladder and kidney diseases, metabolic and urological disorders, insomnia, and neurological deterioration. Although the chemistry of some sulfur mineral bath water is published and/or otherwise available, some commercial mineral springs still advertise an absence of the sulfur odor reflecting little understanding among mineral spring/therapeutic spa providers of the recently published beneficial effects of $H_2S$.

The short and long term preservation of living biological material such as cultured cells, stem cells, and whole organs is essential for the use of this material in research and clinical applications such as transplantation. Preservation solutions and methods are designed to limit oxidative damage and loss of viability. Although $H_2S$ is produced endogenously, serving to protect cellular redox balance, compromised redox regulatory pathways in isolated cells or organs can be augmented by the exogenous addition of $H_2S$. A sulfide bath designed to expose biological material to specific $H_2S$ concentration during preservation procedures could be used to enhance the viability of preserved samples.

SUMMARY OF THE INVENTION

Natural sulfur mineral springs, resulting from deep geothermal activity, are found in specific places around the globe and have been visited for centuries by local cultures without a thorough understanding of cellular $H_2S$ chemistry. Unfortunately, these springs are often too remotely located and/or exclusive for all but a few to enjoy their benefits. Using published chemical recipes of natural mineral springs for many locations worldwide, as well as by making additional measurements, it is possible to initially duplicate the mineral content of any natural sulfur spring without much difficulty. However, a central ingredient of sulfur springs, $H_2S$, is only present naturally as a result of continuous input of geothermally processed water. Without continuous input, $H_2S$ is rapidly oxidized by oxygen to sulfite, sulfate or sulfur, none of which can provide the redox benefit of $H_2S$. Therefore to maintain $H_2S$ concentration in a man-made sulfur spa, a highly controlled amount of $H_2S$ must be continually added.

In view of the foregoing, it is an object of the present invention to both duplicate and maintain the unique chemical composition of these springs using readily-obtainable minerals in a man-made sulfur spa. An apparatus for replicating a sulfur spa according to the present invention is thereby able to accurately replicate exotic warm sulfur springs, making the long term benefits of sulfur balneotherapy available to the public at large, at virtually any location. For instance, Applicants believe that the oxidative stress endured by all humans as a result of aging could be substantially lessened with regular sulfur balneotherapy sessions. This therapeutic regime would serve to augment natural $H_2S$ production thereby restoring and maintaining a more balanced cellular redox state.

Although $H_2S$ is produced endogenously, serving to protect cellular redox balance, compromised redox regulatory pathways in isolated cells, tissues or organs can be augmented by the exogenous addition of $H_2S$. A sulfide bath designed to expose biological material to specific $H_2S$ concentration during preservation procedures could be used to enhance the viability of preserved samples. Accordingly, another object of the present invention is to establish and maintain a sulfide bath for containing tissues, organs, and/or other biological material, allowing the viability of the biological material to be preserved for extended periods.

According to an embodiment of the present invention, an apparatus for establishing a sulfide bath includes a sulfide supply means for introducing sulfide into water for a water bath, a water chemistry monitoring means for monitoring at least a sulfide concentration of water from the water bath, an electronic controller connected with the sulfide supply means and the water chemistry monitoring means, wherein the electronic controller is configured to control the sulfide supply means to regulate the sulfide concentration in the water bath based on input from the water chemistry monitoring means.

According to an aspect of the present invention, the sulfide supply means includes a sulfide salt stock.

According to another aspect of the present invention, the sulfide supply means includes a sulfide gas introduction means for introducing gas into water for the water bath from a sulfide gas source.

According to a further aspect of the present invention, the sulfide supply means further includes a sparging system for removing oxygen from the water into which the sulfide gas is introduced.

According to an additional aspect of the present invention, the sulfide gas introduction means includes a gas equilibration system having an equilibration vessel.

According to another aspect of the present invention, the sulfide gas introduction means includes a static mixer and a gas injector connected with the sulfide gas source.

According to a further aspect of the present invention, the sulfide gas introduction means includes a static gas dispersal system.

According to another embodiment of the present invention, a portable apparatus for establishing a sulfide bath includes a sulfide supply means for introducing sulfide into water for a water bath, a water chemistry monitoring means for monitoring at least a sulfide concentration of water from the water bath, and an electronic controller connected with the sulfide supply means and the water chemistry monitoring means, wherein the sulfide supply means includes at least one fluid conduit for insertion into the water bath, through which fluid conduit the sulfide is introduced, the water chemistry monitoring means includes a sensor package for at least partial immersion in the water bath, and the electronic controller is configured to control the sulfide supply means to regulate the sulfide concentration in the water bath based on input from the water chemistry monitoring means.

According to a further embodiment of the present invention, an apparatus for preserving biological materials in a sulfide bath includes a substantially enclosed water bath for holding the biological materials, a sulfide supply means for introducing sulfide into water for water bath, a water chemistry monitoring means for monitoring at least a sulfide concentration of water from the water bath, a water circulation arrangement for circulating water through the water bath, and an electronic controller connected with the sulfide supply means, the water chemistry monitoring means, and the water circulation arrangement, wherein the electronic controller is configured to control the sulfide supply means to regulate the sulfide concentration in the water bath based on input from the water chemistry monitoring means.

These and other aspects, advantages, and variations on the present invention will be better understood in view of the drawings and following detailed description.

DETAILED DESCRIPTION OF THE PREFERRED EMBODIMENTS

Figure 1:
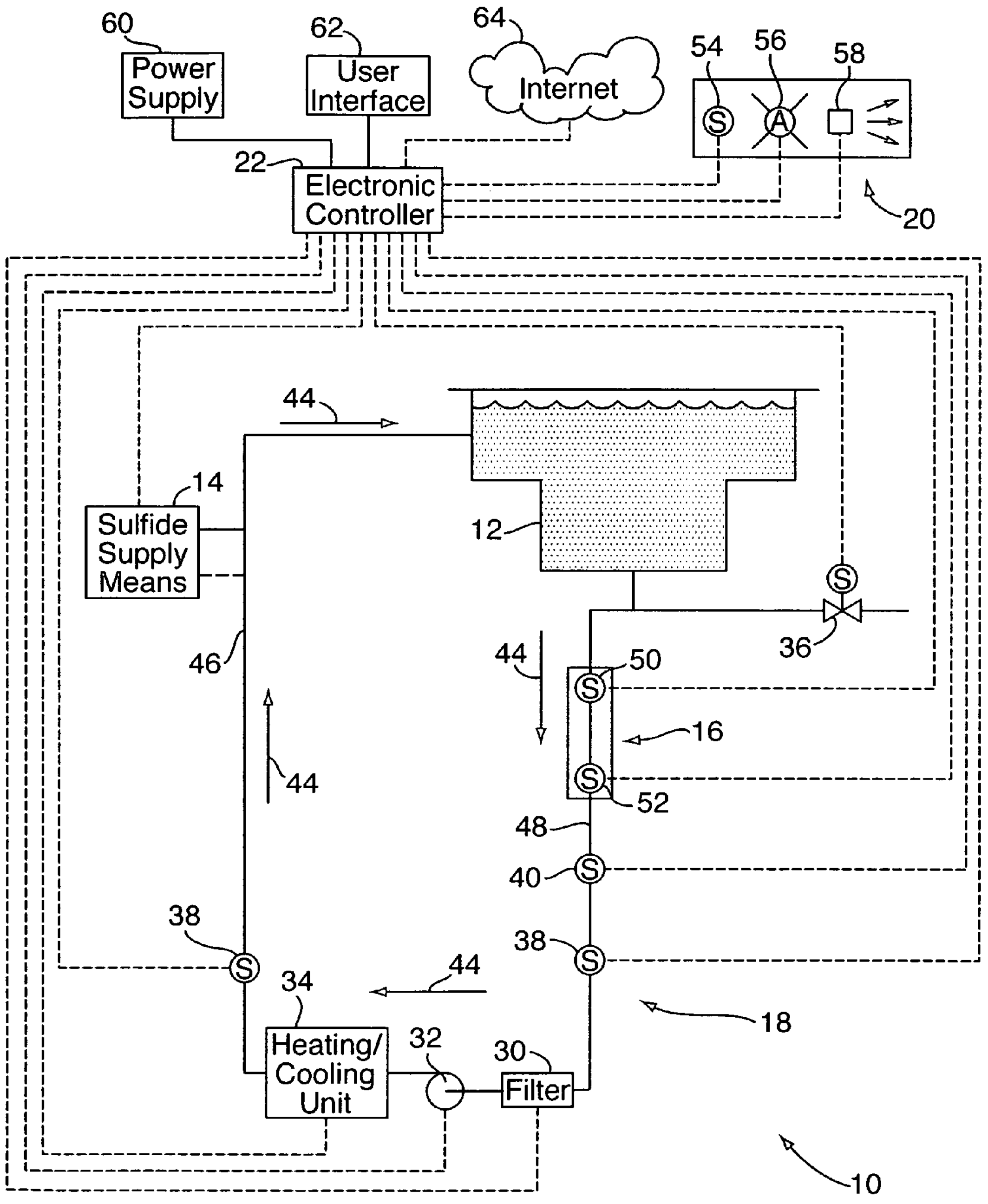
FIG. 1 is a schematic view of an apparatus for establishing a sulfide bath including a sulfide supply means, according to an embodiment of the present invention.

Referring to FIG. 1, an apparatus 10 for establishing a sulfide bath includes a water bath 12, a sulfide supply means 14 for introducing $H_2S$ into water for the water bath 12, and a water chemistry monitoring means 16 for monitoring various chemical properties of water from the water bath 12. A water circulation arrangement 18 circulates and conditions water from the water bath. An airspace $H_2S$ warning and mitigation means 20 detects the $H_2S$ gas concentration in the airspace in the vicinity of the water bath 12, alerts users of the apparatus 10 to potential problems, and enables various measures to mitigate an unsafe $H_2S$ gas concentration. An electronic controller 22 is connected with the sulfide supply means 14, the water chemistry monitoring means 16, the water circulation arrangement 18 and the airspace $H_2S$ warning and mitigation means 20, controlling and/or receiving inputs from various components, as will be explained in detail below.

The water circulation arrangement 18 includes a filter 30, a recirculation pump 32, a heating/cooling unit 34, and a solenoid operated drain valve 36. The heating/cooling unit 34 serves as a temperature modification means allowing for regulation of the temperature of water in the water bath 12. The recirculation pump 32, the heating/cooling unit 34 and the drain valve 36 are connected to the electronic controller 22, allowing for control of these components 32, 34 by the electronic controller 22. The water circulation arrangement 18 also includes flow sensors 38 and a temperature sensor 40, which sensors 38, 40 send inputs to the electronic controller 22 proportional to the parameters sensed.

The sulfide supply means 14 and the water chemistry monitoring means 16 are in fluid communication with the water bath 12 through the water circulation arrangement 18. The general direction of water flow through the water circulation arrangement 18 is indicated by arrows 44. The sulfide supply means 14 takes a suction from and/or discharges to a return leg 46 of the water circulation arrangement 18, and the water chemistry monitoring means 16 are arranged in a suction leg 48 of the water circulation arrangement 18. The suction leg 48 is connected to the water bath 12 at a physical remove from the return leg 46 to ensure that water passing through the water chemistry arrangement 16 is representative of water in the water bath 12, and not disproportionately affected by the concentration of chemicals, such as $H_2S$, in water entering the water bath 12 from the return leg 46.

The water chemistry monitoring means 16 includes an $H_2S$ sensor 50 for monitoring the $H_2S$ concentration in water from the water bath 12 and a pH sensor 52 for monitoring the pH of water from the water bath 12. Both sensors 50, 52 provide inputs to the electronic controller 22 proportional to the parameters sensed.

The airspace $H_2S$ warning and mitigation means 20 includes an airspace $H_2S$ sensor 54, an alarm unit 56, and a ventilation unit 58. The airpace $H_2S$ sensor 54 detects the $H_2S$ gas concentration in the airspace in the vicinity of the water bath 12, the alarm unit 56 generates a sensible warning, preferably audible and/or visible, and the ventilation unit 58 is operable to ventilate the airspace surrounding the water bath 12. For example, the ventilation unit 58 can include a fan that takes a suction on the airspace surrounding the water bath 12 and exhausts to the outside. The airspace $H_2S$ sensor 54 inputs $H_2S$ gas concentration to the electronic controller 22, and the alarm and ventilation units 56, 58 are controllable by the electronic controller 22.

The electronic controller 22 receives power from a power supply 60, that is preferably conditioned and includes a standby power source, such as a battery. The electronic controller 22 has a user interface 62 including an information display, such as an LCD display, and user controls, such as on/off switches, and emergency off switch, programmable timers, and the like. The electronic controller 22 is also connected to the Internet 64, or other network, to enable remote monitoring and/or manual control of the apparatus 10.

In operation, the apparatus 10 is started by a command from the electronic controller 22. The recirculation pump 32 runs to substantially continuously circulate water from the water bath through the filter 30 and the heating/cooling unit 34. The temperature sensor 40 detects the temperature of water in the suction leg 48 and inputs a proportional temperature signal to electronic controller 22. Based on the input from the temperature sensor 40, the electronic controller operates the heating/cooling unit 34 as necessary to regulate the temperature of the water bath 12 water.

The $H_2S$ sensor 50 substantially continuously monitors the $H_2S$ concentration of water from the water bath 12 in the suction leg 48 and inputs the $H_2S$ concentration to the electronic controller 22. As oxidation and/or evaporation of the $H_2S$ in the water bath 12 and circulation arrangement 18 removes $H_2S$ from the water, the electronic controller 22 controls the sulfide supply means 14 to introduce additional $H_2S$ into the water. The water with $H_2S$ added will enter the water bath 12 through the return leg 46 of the water circulation arrangement 18. The additional $H_2S$ will disperse throughout the water in the water bath 12, resulting in a higher $H_2S$ concentration being detected by the $H_2S$ sensor 50. When the $H_2S$ concentration reaches the desired level, the electronic controller 22 will control the sulfide supply means 14 to stop the introduction of $H_2S$ into the water. This process will be repeated when the $H_2S$ concentration falls below a predetermined range, until operation of the apparatus 10 is discontinued.

Flow sensors 38 will substantially continuously monitor the flow present in the recirculation arrangement 18 and input this flow information to the electronic controller 22. In the event a problem with the water circulation arrangement 18 results in an unacceptable reduction of flow through the recirculation arrangement 18, water in the vicinity of the $H_2S$ sensor 50 may not be representative of the $H_2S$ concentration in the water bath 12. The unrepresentative $H_2S$ concentration can lead to inaccurate control of the sulfide supply means 14 by the electronic controller 22. Accordingly, if the flow sensors 38 indicate an unacceptably low flow level to the electronic controller 22, the electronic controller 22 will not direct the sulfide supply means 14 to introduce additional $H_2S$ into water for the water bath 12, or will direct the sulfide supply means 14 to stop the introduction of $H_2S$ if introduction has already begun. Through the user interface 62 and/or the internet 64, the electronic controller 22 will notify the appropriate personnel of the potential problem.

Simultaneously with the operation of the sulfide supply means 14 and the water circulation arrangement 18, the electronic controller 22 is receiving a substantially continuous input of the airspace $H_2S$ gas concentration from the airspace $H_2S$ sensor 54. If the $H_2S$ gas concentration exceeds one or more predetermined limits, the electronic controller 22 directs various actions to mitigate and/or warn users and service personnel of the potential danger. The actions directed by the electronic controller 22 include operating, or increasing the rate and/or capacity of operation, of the ventilation unit 58 to reduce the $H_2S$ gas concentration in the vicinity of the water bath 12, directing the sulfide supply means 14 to stop the introduction of $H_2S$ in water for the water bath 12 if in progress, and activating the alarm unit 56. The electronic controller 22 also notifies appropriate personnel through the user interface 62 and/or the internet 64.

Figure 2:
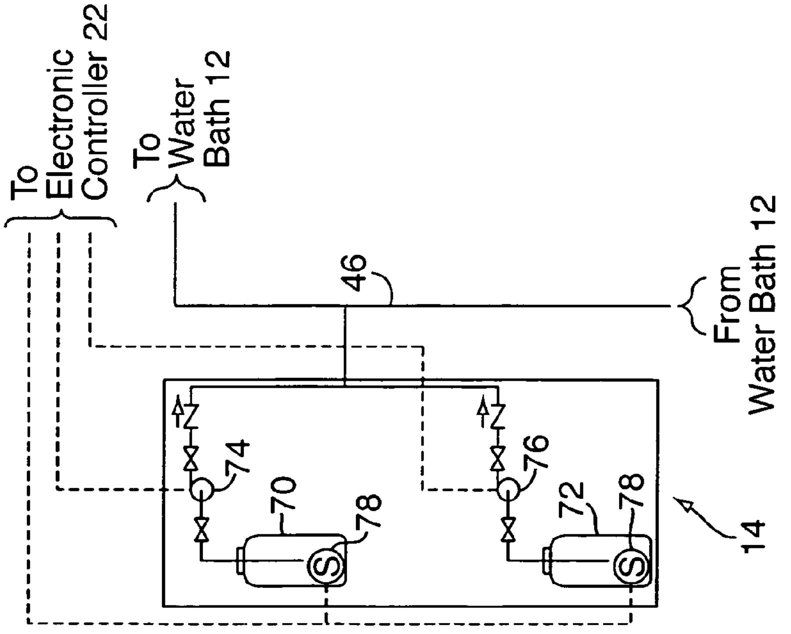
FIG. 2 is a schematic view of the sulfide supply means of FIG. 1, according to an aspect of the present invention.

Referring to FIG. 2, according to an aspect of the present invention, the sulfide supply means 14 includes a $Na_2S$ anoxic stock 70 and a carbonic acid stock 72. A $Na_2S$ addition pump 74 and a carbonic acid addition pump 76 are also included for pumping the $Na_2S$ anoxic stock 70 and the carbonic acid stock 72 to the return leg 46. Together, the carbonic acid stock 72 and the carbonic acid addition pump serve as a pH agent addition means. The pumps 74, 76 are controlled by the electronic controller 22, and stock level sensors 78 input the amount of stock remaining to the electronic controller 22.

In operation, the electronic controller 22 directs the introduction of $H_2S$ into water for the water bath 12 by controlling the $Na_2S$ addition pump 74 to pump the $Na_2S$ anoxic stock into the return leg 46. The $Na_2S$ introduces $H_2S$ into the water for the water bath 12 according to the following reactions:

$$2Na^{+}+S^{-2}+2H \rightarrow HS^{-}+H^{+} \leftrightarrow H_2S$$

The pK for the $H_2S/HS^-$ couple is 6.9 so that at neutral pH or physiological pH, more $HS^-$ than $H_2S$ exists in solution. The pK for the $HS^-/S^{-2}$ is quite alkaline at 14, indicating that $S^{-2}$ concentration is negligible at neutral or physiological pH of approximately 7.3. The alkaline $S^{-2}$ will absorb $H^+$ from solution, thereby raising the pH of water in the water bath 12.

This increase in pH will be detected by the pH sensor 52 (see FIG. 1) and inputted to the electronic controller 22. To restore the pH of water bath 12 water to a more neutral level, the electronic controller 22 will operate the carbonic acid addition pump 76 to add the carbonic acid stock 72 to the return leg 46. The carbonic acid acts a pH agent, lowering pH according to the following reactions:

$$H_2CO_3 \rightarrow HCO_3^{-}+H^{+} \leftrightarrow CO_2+H_2O$$

The pK for the $H_2CO_3/HCO_3$— is 3.6 and the pK for the $HCO_3^-/CO_2$ is 6.2. The $CO_2$ is removed from the water bath 12 by evaporation. These operations will repeat as necessary during the operation of the apparatus 10.

If operation of the apparatus 10 continues for a sufficiently extended duration, the $Na_2S$ anoxic stock 70 and the carbonic acid stock 72 will eventually become depleted. The stock level sensors 78 will input this condition to the electronic controller 22. The electronic controller 22 will notify the appropriate personnel through the user interface 62 and/or the internet 64.

Because $H_2S$ gas can be highly toxic above certain limits, the use of a $Na_2S$ anoxic stock is a relatively safe and simple way to introduce $H_2S$ into water for the water bath 12. However, $Na_2S$ is a relatively inefficient means for introducing $H_2S$ into water, since by weight, sulfide constitutes only a small percentage of $Na_2S$, as it is commercially available, primarily as $Na_2S.9H_2O$. Therefore, most of the weight of the $Na_2S$ salt used to prepare the anoxic stock is water. As a result, for applications involving larger water baths 12, the use of a sulfide supply means 14 including a $Na_2S$ anoxic stock requires the acquisition of a significant quantity of $Na_2S.9H_2O$.

With proper precautions, $H_2S$ gas can be safely handled and used, and offers a more efficient means of introducing $H_2S$ gas into water for the water bath 12. Additionally, since dissolved $H_2S$ will be in equilibrium with $HS^-$ and $H^+$ at a pH of 6.9, the alteration of the pH of water bath 12 water is negligible and the addition of pH agent to counteract the pH effects of $Na_2S$ may be eliminated. Accordingly, in another aspect of the present invention, referring to FIG. 3, the sulfide supply means 14 includes a $H_2S$ gas introduction means 80 for introducing $H_2S$ gas into water for the water bath 12 from a compressed $H_2S$ tank 82. The compressed $H_2S$ gas tank 82 serves as a $H_2S$ gas source. A flow controller 84, controlled by the electronic controller 22, regulates the supply of $H_2S$ gas from the $H_2S$ gas source to the $H_2S$ gas introduction means 80.

The $H_2S$ gas introduction means 80 is located in a piping loop 86 that branches off from and rejoins the return leg 46. The piping loop 86 receives water from the water bath 12 through the return leg 46 downstream of the recirculation pump 32 (see FIG. 1), and returns the water, with $H_2S$ added, to the water bath 12 through the return leg 46, rejoining the return leg closer to the water bath 12. The flow of water through the piping loop 86 is supplemented by a booster pump 88.

Figure 3:
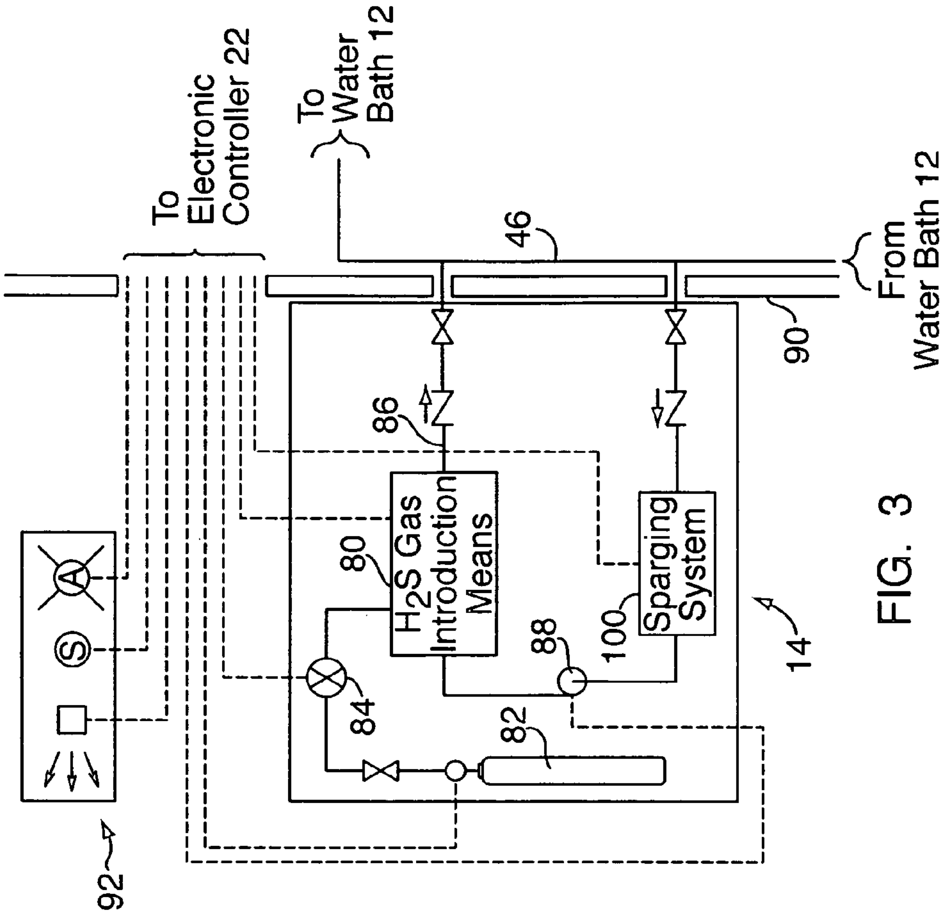
FIG. 3 is a schematic view of the sulfide supply means of FIG. 1 including a $H_2S$ gas introduction means and a sparging system, according to another aspect of the present invention.

Because of the toxic nature of $H_2S$ gas, the $H_2S$ gas introduction means 80 and the $H_2S$ gas source 82 are preferably physically separated from the water bath 12, so that users of the water bath 12 will not be exposed to high $H_2S$ gas concentrations in the event of an inadvertent release of $H_2S$ gas into the atmosphere. In FIG. 3, the physical separation is generally represented by a wall 90. A second airspace $H_2S$ warning and mitigation means 92, connected with the electronic controller 22, substantially identical in structure and operation with airspace $H_2S$ warning and mitigation means 20, is located adjacent to the $H_2S$ gas introduction means 80 and the $H_2S$ gas source 82.

Because the water drawn for the return leg 46 is potentially oxygenated, the efficiency with which the $H_2S$ gas introduction means 80 raises the $H_2S$ concentration of water in the water bath 12 can be adversely effected. This potential adverse effect arises due to the at least partial oxidation of the added $H_2S$, in the piping of the sulfide supply means 14 and the return leg 46, before the water with added $H_2S$ reaches the water bath 12. Because the $H_2S$ gas introduction means 80 is preferably located at some remove from the water bath 12, resulting in a longer length of piping, the adverse effect can be aggravated. Also, because the $O_2$ solubility of water generally increases with decreasing temperature, the adverse effect can also be aggravated in apparatus 10 applications requiring cooler water temperatures.

To mitigate the premature oxidation of $H_2S$, a sparging system 100 is located in the piping loop 86 upstream of the $H_2S$ gas introduction means 80, for deoxygenating water from the water bath 12 before $H_2S$ is added. While the sparging system 100 could be located in the circulation arrangement 18 before the piping loop 86 branches off, this placement would require the deoxygenation of much more water than is ordinarily required by the $H_2S$ gas introduction means 80. To mitigate the premature oxidation of $H_2S$ that could occur once the piping loop 86 rejoins the return leg 46, the piping loop 86 rejoins the return leg 46 proximate to the water bath 12.

Figure 4:
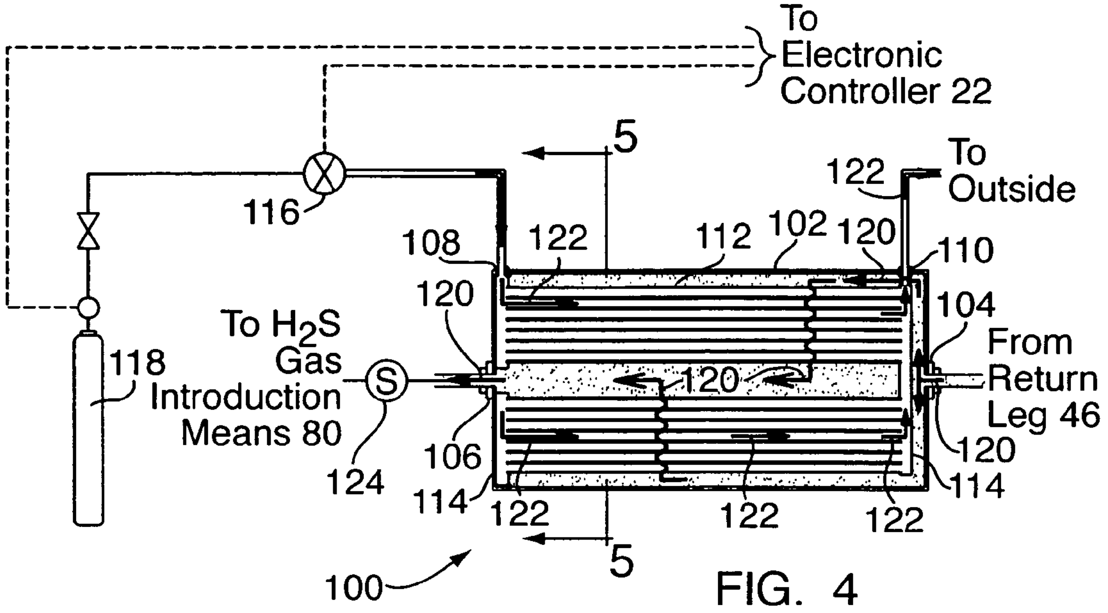
FIG. 4 is a schematic view of the sparging system of FIG. 3 including a sparging vessel, according to a further aspect of the present invention.
Figure 5:
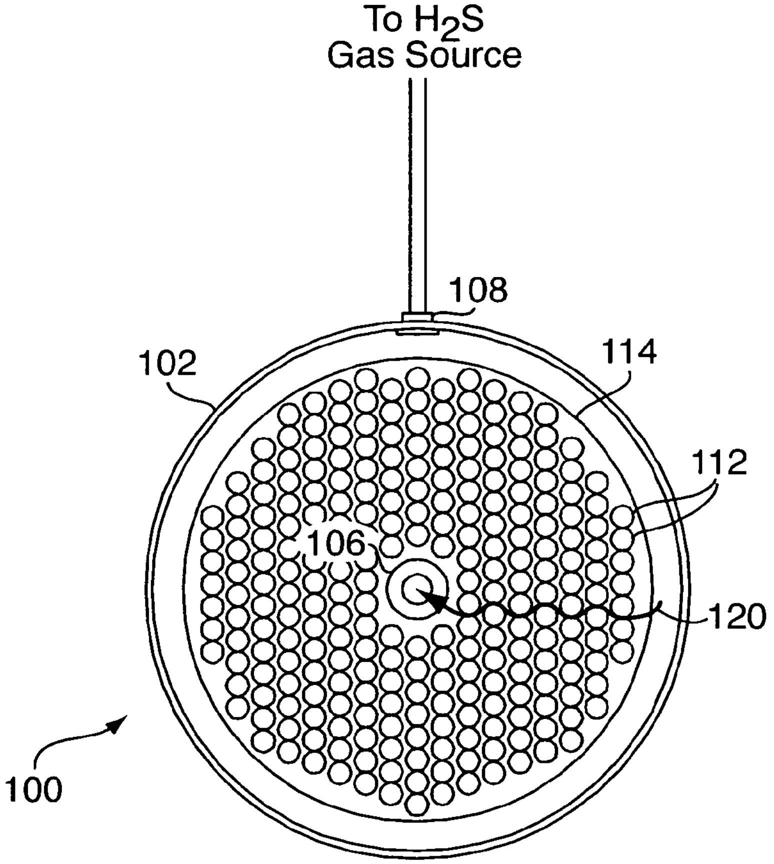
FIG. 5 is a sectional view along line 5-5 of the sparging vessel of FIG. 4.

Referring to FIGS. 4 and 5, according to a further aspect of the present invention, the sparging system 100 includes a sparging vessel 102 having a water inlet 104, a water outlet 106, a sparging gas inlet 108, and a vent 110. Gas tubing 112 is arranged inside the sparging vessel 102, in communication with the gas inlet 108 and the vent 110 through manifolds 114. A flow controller 116 is connected with the electronic controller 22 to regulate flow of a sparging gas from a sparging gas source, such as a compressed nitrogen tank 118, to the sparging gas inlet 108. An $O_2$ sensor 124 downstream of the water outlet 106 monitors the concentration of $O_2$ remaining in the sparging system 100 effluent, and communicates the $O_2$ concentration to the electronic controller 22.

In operation, water from the return leg 46 enters the sparging vessel 102 through the water inlet 104. Due to the manifolds 114, the water cannot pass directly through the sparging vessel to the water outlet 106. Instead, the water is forced to flow around the gas tubing 112, the general direction of water flow being indicated by arrows 120. When $H_2S$ is to be added to the water by the $H_2S$ gas introduction means 80 (see FIG. 3), the electronic controller 22 operates the flow controller 116 to supply $N_2$ gas to the gas tubing 112, the general direction of gas flow being indicated by arrows 122. Depending on the $O_2$ concentration leaving the water outlet 106, the electronic controller 22 further operates the flow controller 116 to raise or lower the $N_2$ gas supply to the gas tubing 112.

The $O_2$ in the water will tend to diffuse through the gas tubing into the $N_2$ gas. The $N_2$ and $O_2$ will then leave the sparging vessel through the vent 110. The $N_2$ and $O_2$ are preferably vented outside to avoid developing high $O_2$ concentrations in the vicinity of the $H_2S$ gas source and, thus, the possible concomitant explosion hazard. The vent 110 is located at the same end of the sparging vessel 102 as the water inlet 104. Likewise, the sparging gas inlet 108 is arranged as the same end of the sparing vessel 102 as the water outlet 106. Accordingly, the flow directions of water and gas through the sparging vessel 102 are substantially opposed, maximizing the diffusion of $O_2$ through the gas tubing into the sparging gas.

Some $H_2S$ will typically remain in the water drawn from the water bath 12 as it is circulated through the piping loop 86. Generally, removing that $H_2S$ from the water would be counterproductive. Accordingly, the gas tubing 112 is formed from a material having a higher permeability to $O_2$ than to $H_2S$. The present inventors have determined that fluorinated ethylene propylene (FEP) is substantially impermeable to $H_2S$, while being more permeable to $O_2$. Because the gas tubing 112 is permeable to $O_2$ but substantially impermeable to $H_2S$, $O_2$ in the water will tend to diffuse through the tubing 112 into the $N_2$ gas, whereas any $H_2S$ remaining in the water will advantageously stay in solution.

When introducing $H_2S$ gas into water for the water bath 12 using the $H_2S$ gas introduction means 80 (see FIG. 3), it is advantageous to ensure that the added $H_2S$ gas is completely dissolved into the water before it reaches the water bath 12. The absence of $H_2S$ bubbles is safer for users, and also makes for easier and more efficient control of $H_2S$ concentration, as $H_2S$ bubbles may be more quickly lost to evaporation upon entering the water bath 12.

Figure 6:
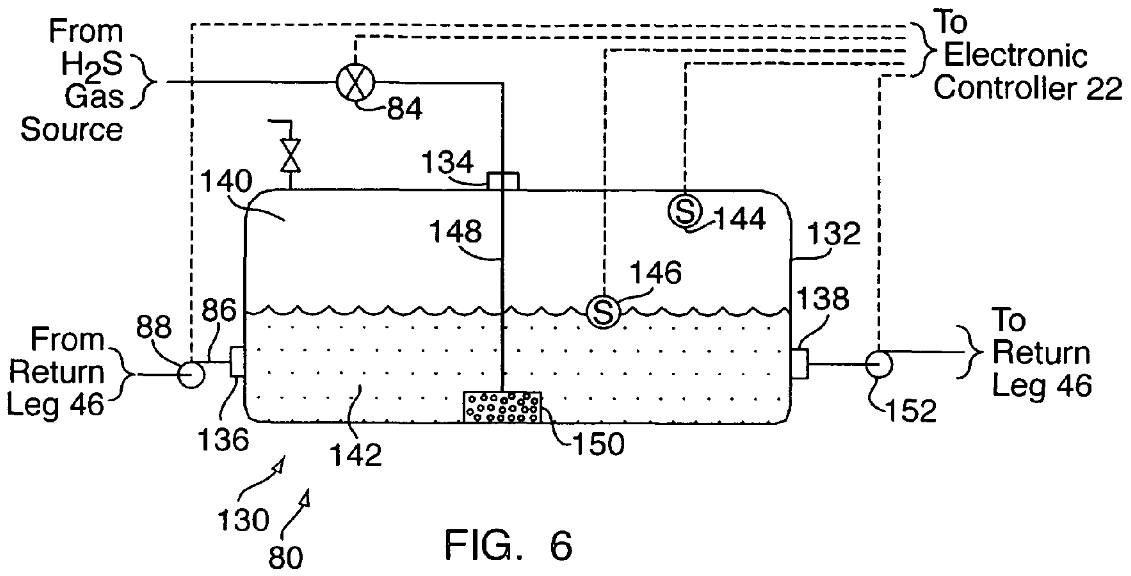
FIG. 6 is a schematic view of the $H_2S$ gas introduction means of FIG. 3 including a gas equilibration system, according to an additional aspect of the present invention.

Accordingly, in an additional aspect of the present invention, referring to FIG. 6, the $H_2S$ gas introduction means 80 includes a gas equilibration system 130. The gas equilibration system 130 includes a gas equilibration vessel 132, having a $H_2S$ gas inlet 134, a water inlet 136 and a water outlet 138. A $H_2S$ gas phase space 140 and liquid phase space 142 are formed within the gas equilibration vessel 132. A pressure sensor 144 and a level sensor 146 respectively input information on pressure of the gas phase space 140 and liquid level of the liquid phase space 142 to the electronic controller 22.

The flow controller 84, controlled by the electronic controller 22, controls the supply of $H_2S$ gas to the gas inlet 134. From the gas inlet 134, $H_2S$ gas travels to the bottom of the gas equilibration vessel 132 through a supply pipe 148, and is bubbled out into the liquid phase space 142 through a gas dispersion chamber 150. The boost pump 88, controlled by the electronic controller 22, controls the introduction of water from the piping loop 86 into the gas equilibration vessel 132 through the water inlet 136. A supply pump 152, controlled by the electronic controller 22, controls the removal of water from the gas equilibration vessel 132 through the water outlet 138 back to the piping loop 86.

In operation, the electronic controller 22 controls the flow controller 84 to introduce $H_2S$ gas at relatively low pressure, approximately 10 psi, to the gas equilibration vessel 132. The $H_2S$ gas exits the gas dispersion chamber 150 and bubbles through the liquid phase space 142 to accumulate in the gas phase space 140. Bubbling the $H_2S$ gas through the liquid phase space 142, rather than directly introducing the $H_2S$ gas into the gas phase space 140, enables quicker absorption of the $H_2S$ gas into solution. When pressure in the gas phase space 140 reaches approximately 5 psi, as detected by the pressure sensor 144, the electronic controller 22 directs the flow controller 84 to stop the flow of $H_2S$ gas to the gas inlet 134.

Under these conditions, $H_2S$ gas will quickly be dissolved into solution in the liquid phase space 142, reaching saturation in approximately 5 minutes. Thus, the liquid phase space 142 will contain a substantially saturated aqueous $H_2S$ solution. When the $H_2S$ concentration detected by the $H_2S$ sensor 50 falls below the desired range, the electronic controller 22 will operate the supply pump 152 to supply the saturated aqueous $H_2S$ solution to the water bath 12 to raise the $H_2S$ concentration to within the desired range. Pumping from the liquid phase space 142 will cause the liquid level in the liquid phase space 142 to drop. This drop in level will be inputted to the electronic controller 22 by the level sensor 146. The electronic controller 22 will operate the boost pump 88 to restore the level in the liquid phase space 142. Absorption of $H_2S$ gas into solution and the level transients will eventually lower the $H_2S$ pressure in the gas phase space 140. As described, the electronic controller 22 will introduce additional $H_2S$ gas to restore the $H_2S$ pressure in the gas phase space 140. These operations will repeat as necessary during the operation of the apparatus 10.

Figure 7:
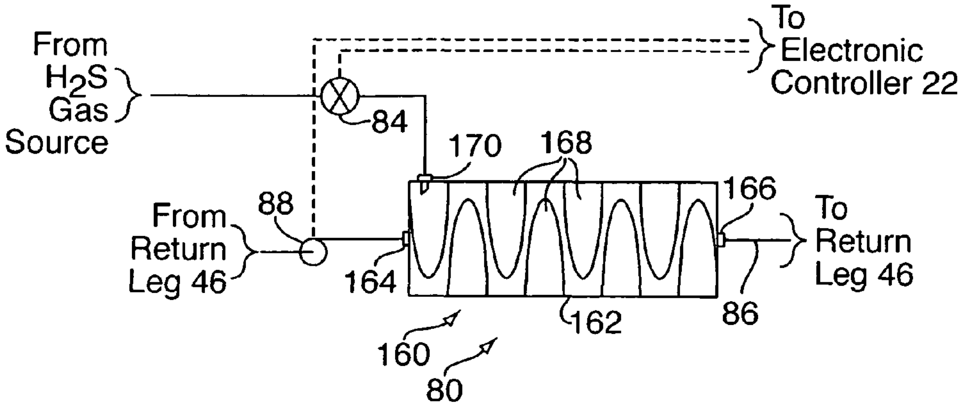
FIG. 7 is a schematic view of the $H_2S$ gas introduction means of FIG. 3 including a static mixing system, according to another aspect of the present invention.

Referring to FIG. 7, according to another aspect of the present invention, the $H_2S$ gas introduction means 80 includes a static mixing system 160. The static mixing system includes a static mixer 162 having a water inlet 164 and a water outlet 166, with a plurality of static mixing elements 168 interposed between the water inlet 164 and outlet 166. A gas injector 170 is arranged proximate to the water inlet, and is connected with the $H_2S$ gas source through the flow controller 84. Water is supplied to the static mixer 162 from the piping loop 86 by the boost pump 88. Thus, by controlling the flow controller 84 and the boost pump 88, respectively, the electronic controller 22 controls the supply of $H_2S$ gas and the supply of water to the static mixer 162.

In operation, when the electronic controller 22 receives an input from the $H_2S$ sensor 50 indicating a low $H_2S$ concentration in water from the water bath 12 (see FIG. 1), the electronic controller 22 operates the flow controller 84 to inject a stream of $H_2S$ gas into the static mixer 162, proximate to the water inlet 164. The electronic controller 22 also operates the boost pump 88 to force water from the return leg 46, via the piping loop 86, through the static mixer 162. The $H_2S$ gas becomes entrained in the flowing water and the static mixing elements 168 repeatedly divide and re-direct the flow of the water and entrained $H_2S$ gas, resulting a rapid mixing action that quickly dissolves the $H_2S$ gas into the water.

The water with dissolved $H_2S$ gas leaves the static mixer through the water outlet 166, returning to the return leg 46 through the piping loop 86, and from the return leg 46 to the water bath 12. The water with dissolved $H_2S$ gas entering the water bath 12 increases the concentration of $H_2S$ gas in the water passing the $H_2S$ sensor 50. Once the $H_2S$ concentration returns to the desired range, the electronic controller 22 controls the flow controller 84 to stop the injection of $H_2S$ gas through the gas injection 170 and stops the boost pump 88. These operations will repeat as necessary during the operation of the apparatus 10.

Figure 8:
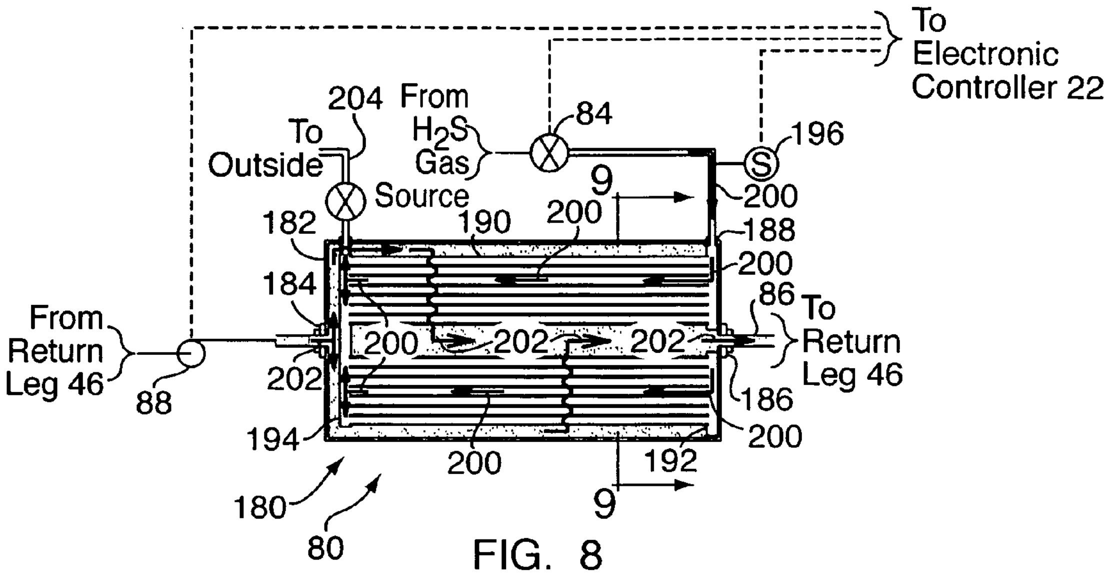
FIG. 8 is a schematic view of the $H_2S$ gas introduction means of FIG. 3 including a static $H_2S$ gas dispersal system having a dispersal vessel, according to a further aspect of the present invention.
Figure 9:
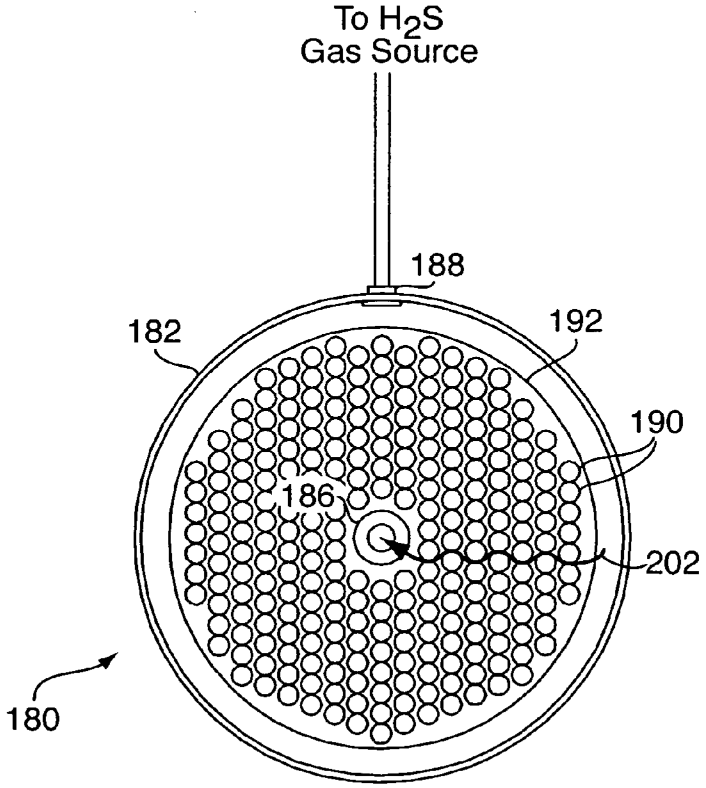
FIG. 9 is a sectional view along line 9-9 of the dispersal vessel of FIG. 8.

Referring to FIGS. 8 and 9, according to a further aspect of the present invention, the $H_2S$ gas introduction means 80 includes a static $H_2S$ gas dispersal system 180. The gas dispersal system 180 includes a dispersal vessel 182 having a water inlet 184, a water outlet 186, and a $H_2S$ gas inlet 188. Gas tubing 190 is arranged within the dispersal vessel 182. Proximate to the water outlet 186, the gas tubing 190 is in communication with the gas inlet 188 through an inlet manifold 192. Proximate to the water inlet 184, the gas tubing terminates at a blind end manifold 194. A pressure sensor 196 monitors the $H_2S$ gas pressure in the downstream of the flow controller 84 and inputs this information to the electronic controller 22. Gas from the $H_2S$ gas source is supplied to the gas inlet 188 through the flow controller 84 and water is supplied to the water inlet 184 by the boost pump 88. Thus, the electronic controller 22 controls the supply of $H_2S$ gas and water to the dispersal vessel 182 by operating, respectively, the flow controller 84 and the boost pump 88.

In operation, when the electronic controller 22 receives an input from the $H_2S$ sensor 50 that the $H_2S$ concentration in water from the water bath 12 (see FIG. 1) is below the desired range, the electronic controller 22 operates the flow controller 84 to pressurize the gas tubing 190 with $H_2S$ gas from the $H_2S$ gas source. The general direction of $H_2S$ gas flow into the tubing 190 is indicated by arrows 200. When the desired $H_2S$ gas pressure is reached, as indicated by the pressure sensor 196, the electronic controller 22 stops $H_2S$ gas flow using the flow controller 84. If contaminant gases build up inside the gas tubing 190, they can be vented outside through a vent line 204.

The electronic controller 22 also initiates flow through the dispersal vessel 182 by operating the boost pump 88 in the piping loop 86. Water from the return leg 46 is directed into the water inlet 184. Due to the blind end manifold 194 and the inlet manifold 192, the water cannot flow directly to the water outlet 186. Instead, the water must flow around the gas tubing 190. The general direction of water flow through the dispersal vessel is indicated by arrows 202. As the water flows around the gas tubing 190, $H_2S$ gas diffuses through the gas tubing 190 and is absorbed into the water. To facilitate the diffusion of $H_2S$ gas through the gas tubing 190, the gas tubing 190 is formed from a material that is highly permeably to $H_2S$. The present inventors have found that polydimethylsiloxane exhibits excellent $H_2S$ permeability.

The water with $H_2S$ added leaves the dispersal vessel 182 through the water outlet 186, and returns to the water bath 12 through the piping loop 86 and the return leg 46. When the $H_2S$ concentration in water from the water bath 12, as detected by the $H_2S$ sensor 50, is restored, the electronic controller 22 will stop the boost pump 88 and stop the pressurization of the gas tubing 190, if in progress. If the supply of water with added $H_2S$ to the water bath 12 continues long enough, diffusion of $H_2S$ gas through the gas tubing 190 will eventually result in $H_2S$ gas pressure dropping below the desired level, as indicated by the pressure sensor 196. The electronic controller 22 will then operate the flow controller 84 as necessary to restore the $H_2S$ gas pressure. These operations will repeat as necessary during the operation of the apparatus 10.

Based on the dimensions and operational characteristics of the apparatus 10, such as the total water capacity, pump flow rates, and temperature range, the electronic controller 22 is configured to operate the $H_2S$ gas introduction means 80 (see FIG. 3) to ensure that no $H_2S$ gas bubbles remain in the water leaving the $H_2S$ gas introduction means 80, while regulating the $H_2S$ concentration of water in the water bath 12.

For example, in the gas equilibration system 130 (see FIG. 6), the electronic controller 22 will not operate the supply pump 152 during the approximately 5 minutes after addition of $H_2S$ gas to the gas phase space 140, to ensure that the $H_2S$ in the liquid phase space 142 has reach equilibrium with the $H_2S$ in the gas phase space 140. In the static mixing system 160 (see FIG. 7), the electronic controller 22 will limit the rate of $H_2S$ gas injection into the static mixer 162 based upon the mixing capabilities of the installed static mixer 162 in view of the dimensions and operational characteristics of rest of the apparatus 10 to ensure that all the injected $H_2S$ gas can be absorbed. In the static $H_2S$ gas dispersal system 180 (see FIG. 8), the electronic controller 22 is configured to establish a $H_2S$ pressure in the gas tubing 190 that, based on the flow through the dispersal vessel 182, will ensure no gaseous $H_2S$ will form in the water as it passes through the dispersal vessel 182.

Figure 10:
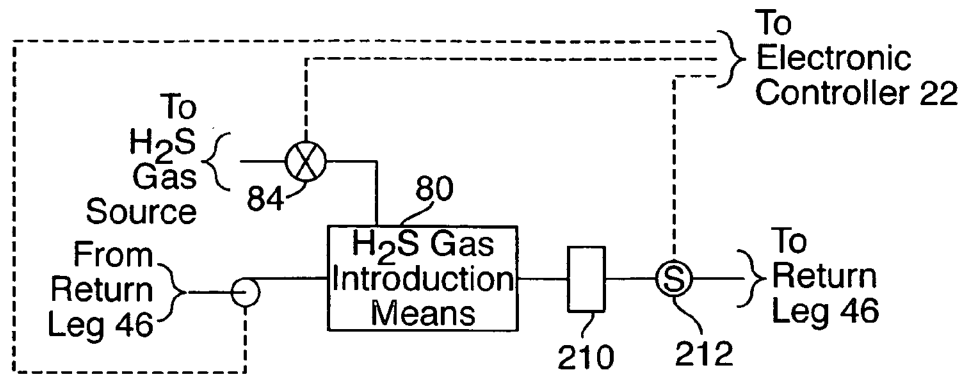
FIG. 10 is a partial schematic view of the sulfide supply means of FIG. 3, including additional components downstream of the $H_2S$ gas introduction means, according to an additional aspect of the present invention.

However, transient conditions may arise altering the rate and/or capacity for water in the $H_2S$ introduction means 80 to absorb $H_2S$ into solution. For example, the simultaneous entry, exit and/or movement of several users from large water bath 12 may result in a significant temperature, $O_2$ concentration, and/or flow transient, which would be aggravated in an apparatus 10 not equipped with a temperature modification means or a sparging system. It is advantageous to equip the apparatus 10 to mitigate the effects of, and/or respond to, such transients. Accordingly, referring to FIG. 10, in an additional aspect of the present invention, a bubble trap 210 and a $H_2S$ supply sensor 212 are between the $H_2S$ gas introduction means 80 and the return leg 46.

In the event of a transient condition resulting in undissolved $H_2S$ gas being present in the $H_2S$ gas introduction means 80 effluent, the bubble trap 210 mechanically prevents the $H_2S$ bubbles from passing, while allowing water with dissolved $H_2S$ to pass. The $H_2S$ supply sensor 212 inputs the $H_2S$ concentration of water leaving the $H_2S$ gas introduction means 80 to the electronic controller 22. The electronic controller 22 is configured to adjust the operation of the $H_2S$ gas introduction means 80 if the $H_2S$ concentration in the effluent is outside of the desired range.

For example, with the gas equilibration system 130, the electronic controller 22 can adjust the time required for equilibration of $H_2S$ between the liquid phase space 142 and the gas phase space 140. With the static mixing system 160, the electronic controller 22 can adjust the flow rate from the boost pump 88, if a variable capacity pump is employed, and/or the rate at which $H_2S$ gas is supplied to the gas injector 170. With the static dispersal system 180, the electronic controller can adjust the flow rate from the boost pump 88 and/or the gas pressure in the gas tubing 190. Thus, the control of the $H_2S$ concentration in water bath 12 water is precise and accurate under a wider range of conditions.

Figure 11:
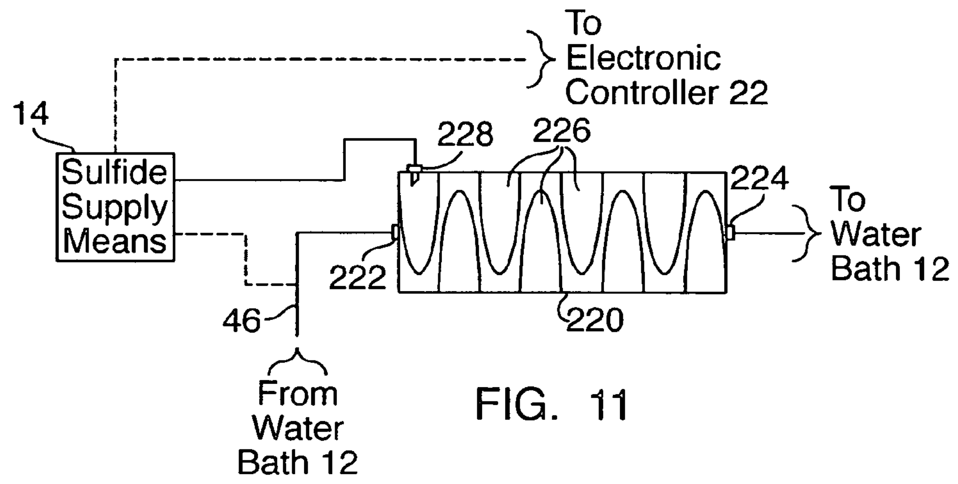
FIG. 11 is a partial schematic view of the apparatus of claim 1, including additional components, according to another aspect of the present invention.

Referring to FIG. 11, to further ensure that the $H_2S$ in water from the sulfide supply means 14 entering the water bath 12 is thoroughly dissolved, and to ensure that the water from the sulfide supply means 14 is evenly mixed with circulated water returning to the water bath 12 from the return leg 46, a static mixer 220 is located in the return leg 46, in another aspect of the present invention. The static mixer 220 has a water inlet 222 and a water outlet 224, with a plurality of mixing elements 226 interposed between the inlet 222 and outlet 224. A fluid injector 228 is arranged proximate to the water inlet 222.

In operation, circulated water from the water bath 12 by the circulation arrangement 18 (see FIG. 1) returns to water bath 12 through the static mixer 220. When the electronic controller 22 directs the supply of $H_2S$ from the sulfide supply means 14, the water from the sulfide supply means 14 is injected into the circulated water entering the static mixer 220 by the fluid injector 228. The combined water is then thoroughly mixed by the static mixing elements 226. The mixed water exits through the water outlet 224 and returns to the water bath 12. As discussed above in connection with the location of the sparging system 100, it is advantageous to locate the static mixer 220 close to the water bath 12 to minimize the time for oxidation of $H_2S$ in the water from the sulfide supply means 14 by $O_2$ in the water in the return leg 46.

Figure 12:
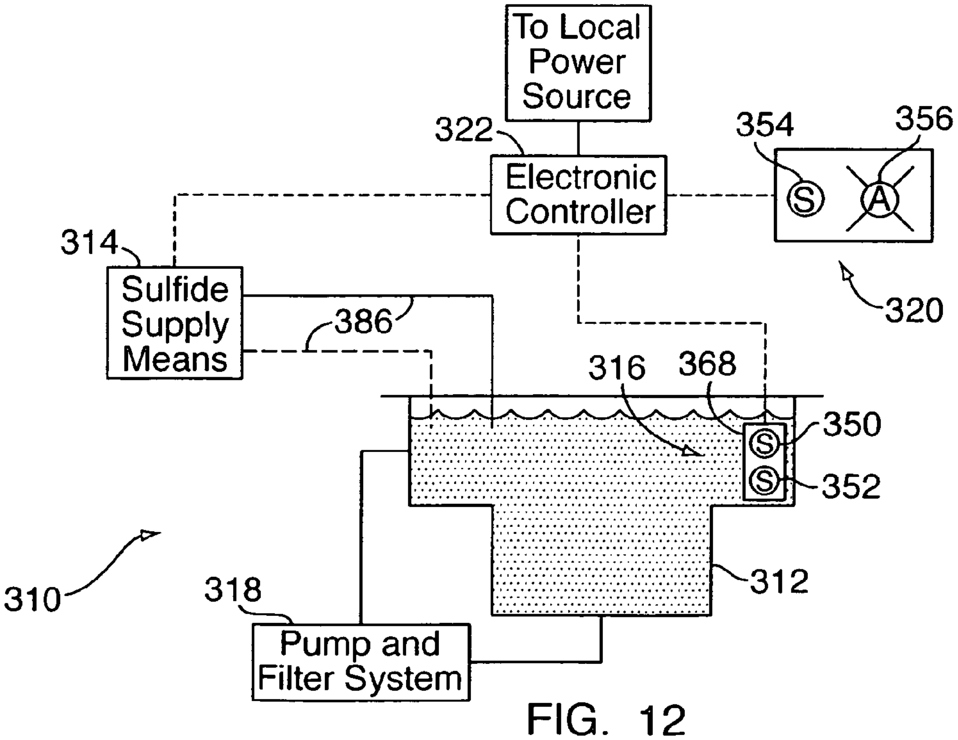
FIG. 12 is a schematic view of an apparatus for establishing a sulfide bath is designed for use in connection with an existing water bath, according to another embodiment of the present invention.

In the embodiment of FIG. 1, the sulfide supply means 14 and water chemistry monitoring means 16 are in fluid communication with the water bath 12 through fixed connection(s) with the water circulation arrangement 18. However, an apparatus for establishing a sulfide bath according to the present invention is not limited to such an embodiment. For example, referring to FIG. 12, in another embodiment of the present invention, an apparatus 310 for establishing a sulfide bath is designed for use in connection with an existing water bath 312. The existing water bath 312 may have its own pump and filter system 318. The apparatus 310 includes a sulfide supply means 314, a water chemistry monitoring means 316, an airspace $H_2S$ warning means 320, and an electronic controller 322, which are all made to be portable and readily transportable between different existing water baths, so as to allow the establishment and maintenance of a sulfide bath in virtually any location with an existing water bath.

The sulfide supply means 314 communicates with the existing water bath 312 through one or more removable fluid conduit(s) 386 that are inserted into water in the existing water bath 312. In general structure and function, the sulfide supply means 314 can be essentially similar to any one of the aspects of the sulfide supply means 14 described above. However, the aspect of FIG. 2, in which the sulfide supply means 14 includes a $Na_2S$ anoxic stock 70 is particularly advantageous for portable applications due to its relative safety and simplicity.

The water chemistry monitoring means 316 includes a $H_2S$ sensor 350 and a pH sensor 352, similar to the $H_2S$ sensor 50 and a pH sensor 52 of the water chemistry monitoring means 16. For use with the existing water bath 312, the sensors 350 and 352 are included in a sensor package 368 for immersion in the existing water bath 312. The airspace $H_2S$ warning means 320 includes an airspace $H_2S$ sensor 354 and alarm unit 356, substantially similar to the sensor 54 and alarm unit 56. The electronic controller 322 is adapted for connection to a local power source.

In operation, the sulfide supply means 314, water chemistry monitoring means 316, airspace $H_2S$ warning means 320 and electronic controller 322 are brought to the desired usage location and unpacked. The existing water bath 312 is filled and the pump and filter system 318 is operated in accordance with its operating instructions. The conduit(s) 386 from the sulfide supply means 314 are inserted into the water of the water bath 312. If two conduit(s) 386 are used, as a supply and a return, the conduits 386 are preferably spaced apart from one another. The sensor package 368 is immersed in the water of the water bath 312, preferably at a remove from the conduits 386. The airspace $H_2S$ warning means 320 is placed in a suitable location to sample the air in the vicinity of the water bath 312, and the electronic controller 322 is connected to the local power source.

Once operation of the apparatus 310 begins, regulation of $H_2S$ concentration in the water of the water bath 312 proceeds substantially as described above. In the event, an unacceptably high airspace $H_2S$ concentration is detected by the airspace $H_2S$ sensor 354, the electronic controller stops the introduction of $H_2S$ by the sulfide supply means 314 and/or activates the alarm unit 356. Once operation of the apparatus 310 is no longer desired, power to the electronic controller 322 is disconnected, fluid conduit(s) 386 and the sensor package 368 are removed, and the apparatus 310 is re-packed for relocation.

Figure 13:
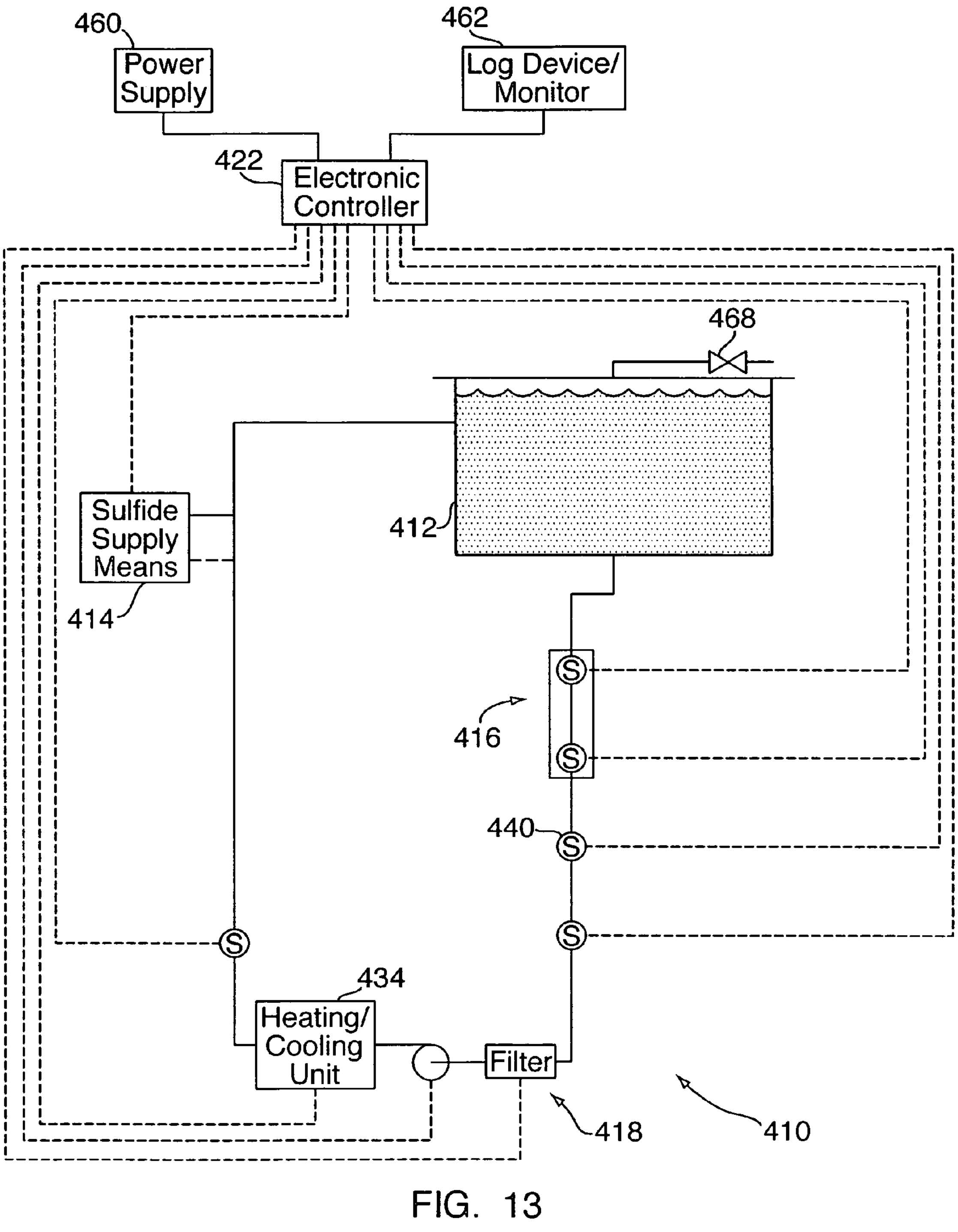
FIG. 13 is a schematic view of apparatus for establishing a sulfide bath including a substantially enclosed water bath, according to a further embodiment of the present invention.

In addition to the therapeutic benefits of $H_2S$ for users of a sulfide bath, $H_2S$ is also capable of preserving the viability of live tissue, as is necessary for various types of scientific research and in connection with organ or tissue transplantation. Aqueous $H_2S$ in a sulfide bath in particular allows for rapid absorption by cells. Thus, tissues or entire organs could be quickly permeated with $H_2S$, more completely and rapidly preserving the organ. Accordingly, referring to FIG. 13, in a further embodiment of the present invention, an apparatus 410 for establishing a sulfide bath includes a substantially enclosed water bath 412, dimensioned to accommodate live organs or tissues. The enclosed water bath 412 includes a relief valve 468 to vent any excess gases that accumulate in the water bath 412. Water added to the water bath 412 preferably includes a physiological buffer, having a pH of approximately 7.3, or another pH optimized for the particular cells, tissues, or organs.

The apparatus also includes a sulfide supply means 414, a water chemistry monitoring means 416, a water circulation arrangement 418 and an electronic controller 422. The sulfide supply means 414 can introduce $H_2S$ as in any one of the aspects of the present invention described above in connection with sulfide supply means 14. The water chemistry monitoring means 416 is substantially similar to the water chemistry monitoring means 16, and the water circulation arrangement 418 is substantially similar to the water circulation arrangement 18. The electronic controller 422 is connected with a power supply 460 that is primarily battery operated for portability, but preferably can connect to various local power supplies, including 12 volt vehicular power supplies. The electronic controller 422 is also connected with a log device/monitor 462, allowing scientific or medical personnel to track and monitor the conditions in the water bath 412, and the status of the tissues contained therein.

The operation of the electronic controller 422 in connection with the sulfide supply means 414, the water chemistry monitoring means 416, and the water circulation arrangement, to maintain the desired $H_2S$ concentration in the water in the water bath 412 is substantially similar to the operation of the electronic controller 22 in connection with the similar components in the embodiments and aspects described above, except as noted. For use in connection with preserving organs for transplantation, all components of the apparatus 410 are dimensioned to be readily transportable. For example, the apparatus 410 should be able to fit in a standard ambulance, medical helicopter and/or truck, and be light enough for carriage by a pair of medical support personnel.

In addition to regulating the $H_2S$ concentration in the water bath 412, the electronic controller 422 is configured to operate the temperature modification means 434, based on input from the temperature sensor 440, to maintain the temperature of water in the water bath 412 lower than the normal body temperature of the tissue stored in the water bath 412. The use of depressed temperatures will further slow the metabolism and extend the viability of the stored tissues. In addition to use in connection with the temporary preservation of living tissue for scientific purposes and in connection with organ transplantation, the apparatus 410 can be used in connection with the indefinite preservation of tissue that is to be frozen. Prior to freezing, the tissue to be frozen would be gradually chilled in the water bath 412, while absorbing the $H_2S$ from the water. The tissue could then be removed and frozen, or frozen while remaining in the water bath 412.

The present invention is not limited to the embodiments and aspects shown and described. Instead, various modifications and adaptations to particular circumstances can be made while remaining within the scope of the present invention.

For example, the term "water bath" as used herein refers generically to a structure suitable for containing water and a person or some other object, such as an organ or tissues, at least partially immersed therein, and does not necessarily refer to such a structure together with the water with which it is filled. Furthermore, "organs" and "tissues" are not limited to a particular species, or size or extent of biological matter. Instead, the terms are used generically to refer to any biological specimen or preparation used in scientific research or in medical applications.

The term "sulfide" as used herein is not necessarily limited to the particular species $H_2S$, but includes the sulfide species $H_2S$, $HS^-$, $S^{-2}$, unless otherwise specified. Additionally, the present invention is not limited to the particular aspects of the sulfide supply means 14, 314, 414 described herein. For instance, other sulfide salts besides $Na_2S$ could be employed, such as NaHS. Additionally, other sulfide containing gases other than $H_2S$ could be used. The sulfide supply means could also include the supply of waters that naturally contain sulfide, controlled by the electronic controller 22, based on feedback from the water chemistry monitoring means 16.

The present invention is not limited to a establishing a particular $H_2S$ concentration. The $H_2S$ concentration should be optimized for the particular application of the sulfide bath apparatus. However, a sulfide concentration of approximately 200 μM is found in many naturally occurring spas.

In the embodiment described, flow sensors 38 are used to verify flow through the water circulation arrangement 18. However, other suitable flow verification techniques can be used for this purpose, either in addition to, or instead of, the flow sensors 38. For example, a differential pressure cell, measuring the pressure drop across the pump 32 could be used. Also, the operational status of the pump 32 could be verified by ensuring that there is power being supplied to the pump, verifying the speed of the pump, the current through the pump windings, and the like.

In addition to the components described above, the water circulation arrangement 18 can also advantageously include other components used in traditional, non-sulfide spas, such as other sanitation components. However, such components should be suitable for use with water containing dissolved $H_2S$. For instance, it would generally be advantageous to avoid using sanitation components that introduce $H_2S$ scavenging chemicals.

In the water circulation arrangement 18 described above, the piping loop 86 having the sulfide introduction means 14 connects with the return leg 46 upstream of the water bath 12. Piping loop 86 may alternately empty directly into the water bath 12 through a separate connection, rather than rejoining the return leg 46.

The term "electronic controller" can include dedicated electronic control devices, such as a proportional integral derivative (PID) controller, or multi-purpose devices such as a personal computer. Additionally, "electronic controller" does not necessarily specify a unitary device. For instance, a laptop computer used in connection with a separate input/output device qualifies as an "electronic controller." Also, "electronic controller" does not necessarily specify a single control unit. For example, an apparatus in which one control unit controlled the sulfide supply mans, another control unit separately controlled the airspace $H_2S$ mitigation and warning means, and a further control unit was used to control the water recirculation arrangement would still fall within the meaning of the term "electronic controller."

The term "sensor" as is used herein is generic to all types of sensing devices, and is not necessarily limited to sensors providing substantially continuous and/or proportional outputs. Although, in the various sensors described herein are capable of providing substantially continuous proportional inputs to the electronic controller 22. However, other types of sensors can also be employed in connection with the present invention. For instance, a switch, such as a pressure switch, level switch, or temperature switch, providing output signals only at discrete setpoints, can be used in place of a pressure with a continuous, proportional output. Generally, the particular type of sensor should be chosen based on the demands of the particular application and cost considerations.

Similarly, control of the various components by the electronic controller 22 is not limited to a particular control scheme or logic. For instance, the control of $H_2S$ addition by the electronic controller 22 can be a simple ON/OFF control, where a constant addition is directed until a desired $H_2S$ concentration is reached, or the control can be a variable, proportional control, where a variable addition rate is adjusted based on continuous sensor feedback to maintain the $H_2S$ concentration within a given range.

The "connection" between the electronic controller and the sensors and other components is not limited to a particular type of connection. For instance, connections could be direct electrical connections, optical connections, wireless connections, indirect connections through relays or other intermediate components, and the like.

Also, the present invention further includes the use of redundant components to enhance the safety and reliability of operation. For instance, multiple $H_2S$ sensors can be employed with the water chemistry monitoring means 16 to mitigate the impact of a sensor failure. In addition to simple redundancy of components, the electronic controller 22 can be further configured to optimize the effectiveness of the redundant components. For example, if multiple $H_2S$ sensors are employed, the electronic controller 22 can more accurately determine $H_2S$ concentration by averaging the sensor inputs. The electronic controller 22 can also be configured to indicate a sensor or sensors as faulty if the inputs fall outside of a given tolerance from other sensors.

The actions directed by the electronic controller 22 in response to a high $H_2S$ gas concentration in the airspace surrounding the water bath 12 can be taken simultaneously, or incrementally. For example, the electronic controller 22 can direct the ventilation of the airspace upon reaching a first limit, direct the sulfide supply means 14 to stop adding $H_2S$ add a second limit, and activate the alarm unit 56 at a third limit, or one or more of these actions can be taken simultaneously at the same limit. The present invention is also not limited to the particular corrective actions enumerated herein.

The present invention is not limited to a particular pH agent, although pH agents should generally be selected that will not adversely interact with the sulfide in the water bath 12. The carbonic acid stock disclosed is only one option. Preferably, the carbonic acid stock is formed by pressurizing water with $CO_2$ gas, similar to the method used to carbonate beverages. Other weak acid stocks could also be used, or suitably diluted stronger acid stocks. For example, muriatic, or hydrochloric acid (HCl), a strong acid, is frequently used for pH control in swimming pools. Although when the apparatus 10 is equipped with a $H_2S$ gas introduction means no pH transient will occur in connection with the addition of $H_2S$, the controlled addition of pH agent can still be used for other purposes, such as the pH management that is practiced in traditional, non-sulfide baths, or to maintain a different pH for therapeutic, research or medical reasons.

The gas tubing 112 for the sparging system 100, as described above, is preferably formed from fluorinated ethylnene propylene, and the present inventors have also found that polytetrafluoroethylene, and perfluoroalkoxy exhibit suitable impermeability characteristics to $H_2S$, while being permeable to $O_2$. However, the present invention is not necessarily limited to such materials.

The sparging system 100, described above as used in connection with the $H_2S$ gas introduction means. While the sparging system 100 advantageously decreases the $O_2$ concentration of the water to which the $H_2S$ is to be added, configurations without the sparing system 100 also fall within the scope of the present invention. For example, if a gas equilibration system is used without a sparging system, the equilibration time could be lengthened to accommodate the additional oxidation of $H_2S$ due to extra $O_2$ in the water added to the equilibration vessel.

The gas tubing 190 of the static $H_2S$ dispersal system 180 is described as preferably being formed from polydimethylsiloxane, as exhibiting a high permeability to $H_2S$. The present inventors have found that polysiloxanes, generally, are suitable for the static $H_2S$ gas dispersal system, although the present invention is not necessarily limited to such materials.

As the water bath 412 of the apparatus 410 is enclosed, no airspace $H_2S$ warning and mitigation means is described in connection with the apparatus 410, although warning and/or mitigations means could also be included within the scope of the present invention. For example, the water bath 412 could be placed in a ventilation hood to vent any gases venting from the relief valve 468.

These modifications and adaptations are not an exhaustive list. Those skilled in the art will appreciate that further modifications, variations and adaptations also fall within the scope of the invention as herein shown and described.

What is claimed is:

1. An apparatus for establishing a sulfide bath, the apparatus comprising:

a sulfide supply means for introducing sulfide into water for a water bath;

a water chemistry monitoring means for monitoring at least a sulfide concentration of water from the water bath; and an electronic controller connected with the sulfide supply means and the water chemistry monitoring means;

wherein the electronic controller is configured to control the sulfide supply means to regulate the sulfide concentration in the water bath based on input from the water chemistry monitoring means;

wherein the sulfide supply means includes a sulfide gas introduction means for introducing gas into water for the water bath from a sulfide gas source; and wherein the sulfide gas introduction means includes a static mixer and a gas injector connected with the sulfide gas source.

2. The apparatus of claim 1, wherein the water bath is in fluid communication with the sulfide supply means and the water chemistry monitoring means.

3. The apparatus of claim 2, further comprising:

a water circulation arrangement for circulating water from the water bath.

4. The apparatus of claim 3, wherein the sulfide supply means is in fluid communication with the water bath through the water circulation arrangement.

5. The apparatus of claim 4, wherein the water circulation arrangement includes a static mixer, and water from the sulfide supply means is injected into the static mixer to mix with circulated water in the water circulation arrangement before entering the water bath.

6. The apparatus of claim 4, wherein the sulfide supply means connects to the water circulation arrangement proximate to the water bath.

7. The apparatus of claim 3, wherein the water chemistry monitoring means is in fluid communication with the water bath through the water circulation arrangement.

8. The apparatus of claim 1, wherein the sulfide supply means includes at least one fluid conduit for insertion into the water bath, through which fluid conduit the sulfide is introduced.

9. The apparatus of claim 1, wherein the water chemistry monitoring means includes a sensor package for at least partial immersion in the water bath.

10. The apparatus of claim 1, wherein the sulfide supply means includes a sulfide salt stock.

11. The apparatus of claim 10, wherein the sulfide salt stock is a $Na_2S$ stock.

12. The apparatus of claim 10, wherein the sulfide salt stock is substantially anoxic.

13. The apparatus of claim 10, wherein the sulfide supply means further includes a pH agent addition means for introducing a pH agent into the water for the water bath.

14. An apparatus for establishing a sulfide bath, the apparatus comprising:

a sulfide supply means for introducing sulfide into water for a water bath;

a water chemistry monitoring means for monitoring at least a sulfide concentration of water from the water bath; and an electronic controller connected with the sulfide supply means and the water chemistry monitoring means;

wherein the electronic controller is configured to control the sulfide supply means to regulate the sulfide concentration in the water bath based on input from the water chemistry monitoring means;

wherein the sulfide supply means includes a sulfide gas introduction means for introducing gas into water for the water bath from a sulfide gas source; and wherein the sulfide supply means further includes a sparging system for removing oxygen from the water into which the sulfide gas is introduced.

15. The apparatus of claim 14, wherein the sparging system removes oxygen from the water before the sulfide supply means introduces the sulfide into the circulated water.

16. The apparatus of claim 15, wherein the sparging system includes a sparging vessel having tubes formed from a material having a higher permeability to $O_2$ than sulfide.

17. An apparatus for establishing a sulfide bath, the apparatus comprising:

a sulfide supply means for introducing sulfide into water for a water bath;

a water chemistry monitoring means for monitoring at least a sulfide concentration of water from the water bath; and an electronic controller connected with the sulfide supply means and the water chemistry monitoring means;

wherein the electronic controller is configured to control the sulfide supply means to regulate the sulfide concentration in the water bath based on input from the water chemistry monitoring means;

wherein the sulfide supply means includes a sulfide gas introduction means for introducing gas into water for the water bath from a sulfide gas source; and wherein the sulfide gas introduction means includes a gas equilibration system having an equilibration vessel.

18. The apparatus of claim 1, wherein the sulfide gas introduction means includes a static gas dispersal system.

19. The apparatus of claim 18, wherein the static gas dispersal system includes a dispersal vessel having tubes formed from a material permeable to sulfide.

20. The apparatus of claim 2, wherein the water bath is substantially enclosed.

21. The apparatus of claim 1, wherein the apparatus is portable.

22. An apparatus for establishing a sulfide bath, the apparatus comprising:

a sulfide supply means for introducing sulfide into water for a water bath;

a water chemistry monitoring means for monitoring at least a sulfide concentration of water from the water bath;

an electronic controller connected with the sulfide supply means and the water chemistry monitoring means; and an airspace sulfide monitoring means connected with the electronic controller for monitoring an airspace sulfide concentration;

wherein the electronic controller is configured to control the sulfide supply means to regulate the sulfide concentration in the water bath based on input from the water chemistry monitoring means.

23. The apparatus of claim 22, wherein the electronic controller is further configured to control the sulfide supply means to stop the introduction of sulfide if the airspace sulfide concentration exceeds a predetermined limit.

24. The apparatus of claim 22, further comprising:

a ventilation unit connected with the electronic controller, wherein the electronic controller is further configured to operate the ventilation unit to reduce the airspace sulfide concentration if the airspace sulfide concentration exceeds a predetermined limit.

25. A portable apparatus for establishing a sulfide bath, the apparatus comprising:

a sulfide supply means for introducing sulfide into water for a water bath;

a water chemistry monitoring means for monitoring at least a sulfide concentration of water from the water bath; and an electronic controller connected with the sulfide supply means and the water chemistry monitoring means;

wherein the sulfide supply means includes at least one fluid conduit for insertion into the water bath, through which fluid conduit the sulfide is introduced, the water chemistry monitoring means includes a sensor package for at least partial immersion in the water bath, and the electronic controller is configured to control the sulfide supply means to regulate the sulfide concentration in the water bath based on input from the water chemistry monitoring means;

wherein the sulfide supply means includes a sulfide gas introduction means for introducing gas into water for the water bath from a sulfide gas source; and wherein the sulfide gas introduction means includes a static mixer and a gas injector connected with the sulfide gas source.

26. An apparatus for preserving biological materials in a sulfide bath, the apparatus comprising:

a substantially enclosed water bath for holding the biological materials;

a sulfide supply means for introducing sulfide into water for water bath;

a water chemistry monitoring means for monitoring at least a sulfide concentration of water from the water bath;

a water circulation arrangement for circulating water through the water bath; and an electronic controller connected with the sulfide supply means, the water chemistry monitoring means, and the water circulation arrangement;

wherein the electronic controller is configured to control the sulfide supply means to regulate the sulfide concentration in the water bath based on input from the water chemistry monitoring means;

wherein the sulfide supply means includes a sulfide gas introduction means for introducing gas into water for the water bath from a sulfide gas source; and wherein the sulfide gas introduction means includes a static mixer and a gas injector connected with the sulfide gas source.

27. The apparatus of claim 26, wherein the water circulation arrangement includes a temperature sensor and a temperature modification means connected with the electronic controller, and the electronic controller is further configured to regulate the water bath temperature based on input from the temperature sensor.

* * * * *